(12) United States Patent
Grzesek

(10) Patent No.: US 6,422,911 B1
(45) Date of Patent: Jul. 23, 2002

(54) TOY DEVICE USING THROUGH-THE-BODY COMMUNICATION

(75) Inventor: Robert Grzesek, Redondo Beach, CA (US)

(73) Assignee: Mattel, Inc., El Segundo, CA (US)

( * ) Notice: Subject to any disclaimer, the term of this patent is extended or adjusted under 35 U.S.C. 154(b) by 0 days.

(21) Appl. No.: 09/791,014

(22) Filed: Feb. 22, 2001

(51) Int. Cl.[7] ............................................... A63H 30/00
(52) U.S. Cl. ..................... 446/175; 446/26; 446/484; 340/539; 340/573.1
(58) Field of Search .................... 446/26–28, 175, 446/484; 434/335, 336, 338, 340; 340/539, 573.3, 573.1, 573.2, 573.4, 323 R

(56) References Cited

U.S. PATENT DOCUMENTS

| | | |
|---|---|---|
| 3,937,004 A | 2/1976 | Natori et al. |
| 4,063,410 A | 12/1977 | Welling |
| 4,414,537 A | 11/1983 | Grimes |
| 5,014,040 A | 5/1991 | Weaver et al. |
| 5,047,952 A | 9/1991 | Kramer et al. |
| 5,212,372 A | 5/1993 | Quick et al. |
| 5,488,362 A | 1/1996 | Ullman |
| 5,537,102 A | 7/1996 | Pinnow |
| 5,648,753 A | 7/1997 | Martin |
| 5,818,359 A | 10/1998 | Beach |

FOREIGN PATENT DOCUMENTS

EP           0281427 A2 *    7/1988

* cited by examiner

*Primary Examiner*—Jacob K. Ackun
*Assistant Examiner*—Bena B. Miller
(74) *Attorney, Agent, or Firm*—Roy A. Ekstrand

(57) ABSTRACT

A wrist unit includes a transmitting circuit capable of producing coded radio frequency signals. The wrist unit when worn by the user applies the encoded radio frequency signals to the users body and causes the encoded signal to propagate through the users body as a transferring medium. A cooperating device includes a receiving contact which the user touches to impart the body signal. A receiver and decoder within the cooperating device identify the user and enable a gate circuit which in turn opens access to the user of the microprocessor and cooperating circuitry within the unit. In the absence of a code match, the access to the cooperating device is refused.

5 Claims, 2 Drawing Sheets

TOY DEVICE USING THROUGH-THE-BODY COMMUNICATION

FIELD OF THE INVENTION

This invention relates generally to toys and particularly to toys operative in a communications mode.

BACKGROUND OF THE INVENTION

Toys which are capable of communication are well known in the art and have been provided in a variety of formats and designs. Many toys include a plurality of user operated keys or buttons which facilitate inputting and identifying code opening the operation of the device to the user. Still other toys employ locks or closures which restrict access of operation of the toy to a key holder or the like.

In a related art, input devices in the form of gloves or other apparatus are provided with a number of signaling devices which are capable of use in remotely controlling a game or toy apparatus. For example, U.S. Pat. No. 5,488,362 issued to Ullman et al. sets forth an APPARATUS FOR CONTROLLING A VIDEO GAME having a glove-like attachment worn by an operator. The glove includes a wrist portion having parallel conductive contacts. Once set of contacts is connected to a signal generator which produces control signals for characters in a video game. The second set of contacts is connected to the video game. Placing the hand at an angle selectively connects the contacts sending the desired direction control signal to the game.

U.S. Pat. No. 5,212,372 issued to Quick et al. sets forth a PORTABLE TRANSACTION TERMINAL FOR OPTICAL AND KEY ENTRY OF DATA WITHOUT KEYBOARDS AND MANUALLY ACTUATED SCANNERS in which a glove is worn an operator having a plurality of sensors positioned upon the finger and thumb portions of the glove. The sensors are operative in response to movement and flexing of the wearer's fingers and thumb and produce signals which are coupled to a communication device.

U.S. Pat. No. 4,414,537 issued to Grimes sets forth a DIGITAL DATA ENTRY GLOVE INTERFACE DEVICE for translating discreet hand positions into electrical signals representing Alpha-numeric characters. The interface includes a glove having sensors positioned with respect to the hand for detecting the flex of finger joints and sensors for detecting the contact between various portions of the hand. Additional sensors detect the movement of the hand with respect to the gravitational vector.

U.S. Pat. No. 5,537,102 issued to Pinnow sets forth an APPARATUS AND METHOD FOR A SYSTEM CAPABLE OF REMOTELY VALIDATING THE IDENTITY OF AN INDIVIDUAL AND THEIR LOCATION having a wrist worn device which electronically generates a sequence of Pseudorandom numbers that seizes functioning if the band is cut or otherwise opened to detach the device from the individual. A monitoring system remotely validates the continued wearing of the apparatus by the user and allows the wearer to be located remotely.

U.S. Pat. No. 4,063,410 issued to Welling sets forth a DIGITAL WATCH INCLUDING A SIGNAL TRANSMITTER for selective activation of a remote electronic circuit. The wristwatch includes a time of day readout encased in a housing supported by the wrist band. Within the watch housing, time of day display and a signal transmitter are operatively coupled. A receiving station is provided with apparatus for remotely responding to the transmitted signal from the watch to activate an electronic circuit such as a burglar alarm or the like.

U.S. Pat. No. 3,937,004 issued to Natori et al. sets forth a PORTABLE MINIATURE TYPE INFORMATION TREATING DEVICE including an electronic time piece used as a pager watch and having a speaker for emitting an alarm signal at a preset time. The circuit also includes an external call signal responsive to incoming electromagnetic waves.

U.S. Pat. No. 5,014,040 issued to Weaver et al. sets forth a PERSONAL LOCATOR TRANSMITTER adapted to be worn on the wrist and having the size and appearance of a conventional wrist watch. The transmitter is provided with a programmable memory, a transmitter controlled by the memory and an antenna for reliably radiating signals from the transmitter and an automatic alarm actuated by an attempt to remove the unit from the wrist of the wearer.

U.S. Pat. No. 5,047,952 issued to Kramer et al. sets forth a COMMUNICATION SYSTEM FOR DEAF, DEAF-BLIND OR NONVOCAL INDIVIDUALS USING INSTRUMENTED GLOVE the glove supports a plurality of strain gage sensors which respond to flexing movements of the hands. Signals from the circuitry within the glove responsive to the strain gage outputs are amplified and digitized and applied to a computer which includes software for recognition of the hand positions and hand states.

U.S. Pat. No. 5,648,753 issued to Martin sets forth an INTERCHANGEABLE SOUND EFFECT DEVICE which includes means for playing digitally recorded sounds in the form of interchangeable cartridges. The device is designed for use with entertainment and educational-type products such as toys, dolls, figurines, books and instructional guides. The device utilizes an infrared receiver.

U.S. Pat. No. 5,818,359 issued to Beach sets forth a PROCESS AND APPARATUS FOR COMPUTERIZING TRANSLATION OF MOTION OF SUBCUTANEOUS BODY PARTS useful in tracking movement of body parts such as tendons within the carpal tunnel of the wrist.

While the foregoing described prior art devices have to some extent improved the art and have in some instances enjoyed commercial success, there remains nonetheless a continuing need in the art for evermore improved, interesting and amusing toy products which utilize various communication mechanisms.

SUMMARY OF THE INVENTION

Accordingly, it is a general object of the present invention to provide an improved toy device. It is a more particular object of the present invention to provide an improved toy device which utilizes through-the-body communication.

In accordance with the present invention there is provided a toy device comprising: a wrist unit having a housing, a first body contact and a wrist band; a transmitting circuit supported within the housing and having means for generating and coupling an encoded signal to the first body contact; a toy having a second body contact and an operable toy system; and a receiving circuit supported by the toy and having means for receiving and decoding an signal coupled to the second body contact and having decode means for enabling the operable toy system in response to receiving the encoded signal when a user wearing the wrist unit touches the second body contact, the encoded signal being propagated through a users body when wearing the wrist unit.

BRIEF DESCRIPTION OF THE DRAWINGS

The features of the present invention, which are believed to be novel, are set forth with particularity in the appended claims. The invention, together with further objects and advantages thereof, may best be understood by reference to the following description taken in conjunction with the accompanying drawings, in the several figures of which like reference numerals identify like elements and in which:

DESCRIPTION OF THE PREFERRED EMBODIMENTS

Figure 1:
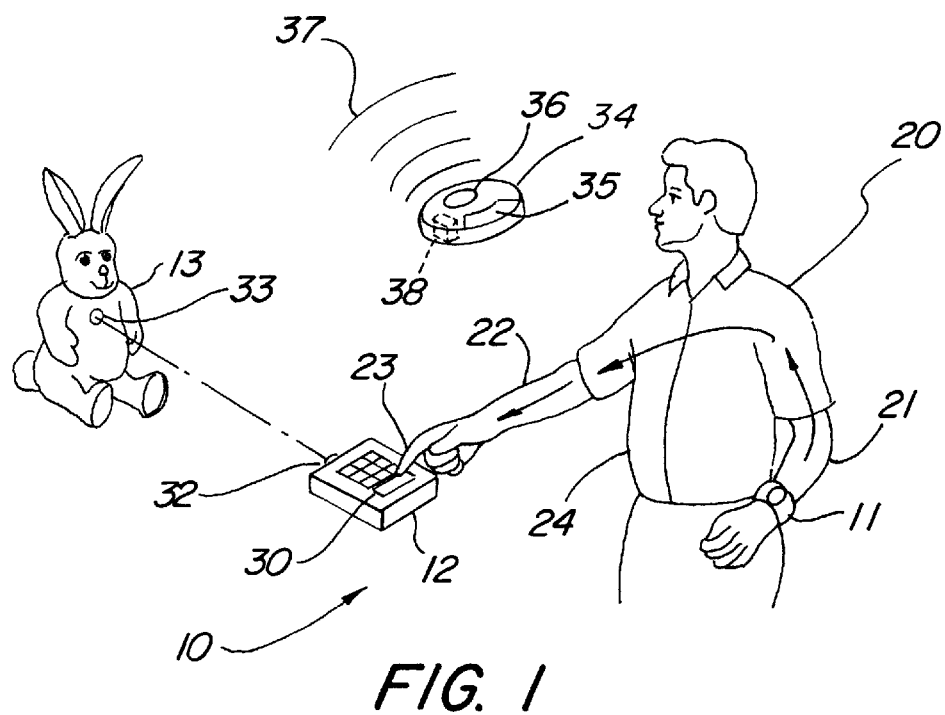
FIG. 1 sets forth a perspective view of a toy device constructed in accordance with the present invention operated by a child user.

FIG. 1 sets forth a perspective view of a toy device constructed in accordance with the present invention and generally referenced by numeral 10. Toy device 10 includes a wrist unit 11, a controlled device 12 and a controlled toy 13. A user 20 is shown wearing wrist unit 11 upon arm 21 while activating device 12 using finger 23 of arm 22. Controlled device 12 includes a housing supporting a contact 30 and a plurality of user operator keys 31. Device 12 further includes an infrared transmitter 32. Controlled toy 13 may be fabricated in accordance with the desired theme or application of the present invention system. In the example shown in FIG. 1, control toy 13 is a small animal figure having an infrared sensor 33. Controlled toy 13 includes internal apparatus (not shown) responsive to sensor 33 in accordance with conventional fabrication techniques.

In operation, and by means described below in greater detail, wrist unit 11 produces a coded signal which is coupled to arm 21 of user 20. Body 24 of user 20 provides a medium through which the signal outputted by wrist unit 11 propagate. The ability of human body to carry electrical signals such as radio frequency signals throughout the body is well known and well established in the art. Suffice it to note here that electrical signals applied by wrist unit 11 to arm 21 appear generally throughout body 24. Of interest with respect to the present invention, is the portion of coupled energy from wrist unit 11 which propagates through arm 21 across body 24 and downwardly through arm 22 to eventually reach finger 13. As the user touches contact 30 with finger 23, a small portion of the signal produced by wrist unit 11 and propagating through body 24 and arm 22 is coupled to contact 30. By means set forth below in greater detail, device 12 responds to the signal coupled to contact 30 to verify that finger 23 is indeed a body portion belonging to the wearer of wrist unit 11. In other words, the encoded signal produced by wrist unit 11 uniquely identifies user 20 to device 12. In the preferred fabrication of the present invention, wrist unit 11 produces a radio frequency signal having an encoded identifier thereon. Further in the preferred fabrication of the present invention, device 12 includes a decoding unit which reads the coded indicator upon the signal received at contact 30 and compares it to a stored reference code to determine whether or not keys 31 of device 12 are to operable in response to user 20.

Control toy 13 is a conventional infrared remote control toy which is provided as an illustration of the use of the present invention toy device. In the example shown in FIG. 1 and provided by device 12, a simple remote control apparatus operable between a remote controlling device 12 and a controlled toy 13 is operable solely by user 20 while wearing wrist unit 11.

By way of further illustration, FIG. 1 also shows an alternative toy 34 having a contract 35 and a speaker grille 36 formed thereon. A conventional sound circuit 38 fabricated in accordance with conventional fabrication techniques responds to the touch of user 20 upon contact 35 to produce an audible sound output which is directed outwardly through speaker grille 36. Thus, the illustration provided by toy device 34 is that of a directly controlled toy in which the encoded signal applied to wrist unit 11 to user 20 is sensed within the toy itself and upon verification that the touch upon contact 35 is that of the wearer of wrist unit 11, toy device 34 is accessed and performs its audible sound production function.

Figure 2:
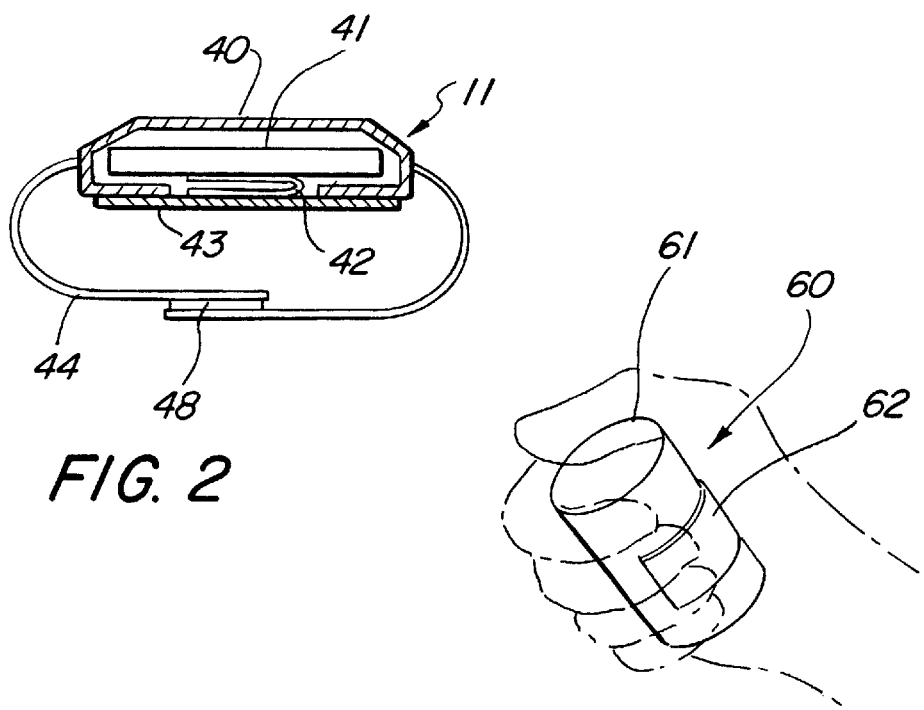
FIG. 2 sets forth a section view of the wrist-worn portion of the present invention toy device.

FIG. 2 sets forth a section view of wrist unit 11. Wrist unit 11 includes a housing 40 within which a circuit 41 is supported. An external contact 43 is positioned upon the underside of housing 40 and is coupled to circuit 41 by a connector 42. A conventional wrist band 44 is secured to housing 40 in a conventional attachment (not shown). Band 44 is used to secure wrist unit 11 to a wearer's wrist in the manner shown in FIG. 1. Band 44 thus includes a cooperating pair of hook-and-loop fabric attachment pads 48. It will be apparent however, that alternative fastening apparatus such as snap fasteners or buckles or the like may be utilized in place of hook-and-loop fabric attachment pads 48 without departing from the spirit and scope of the present invention.

In operation, circuit 41 produces an output signal such as a radio frequency signal which is coupled to contact 43 by connector 42. This signal is preferably encoded with an identifying code recognizable by the cooperating device such as devices 12 and 34 (seen in FIG. 1). Contact 43 is positioned against the wearer's skin to provide optimal signal coupling to the wearer's body and to allow the use of the wearer's body as a propagating medium. Circuit 41 is set forth below in FIG. 3 in greater detail. However, suffice it to note here that circuit 41 is a battery-powered microprocessor based circuit suitable for producing a radio frequency signal of sufficient strength to transmit energy through the wearer's body.

Figure 3:
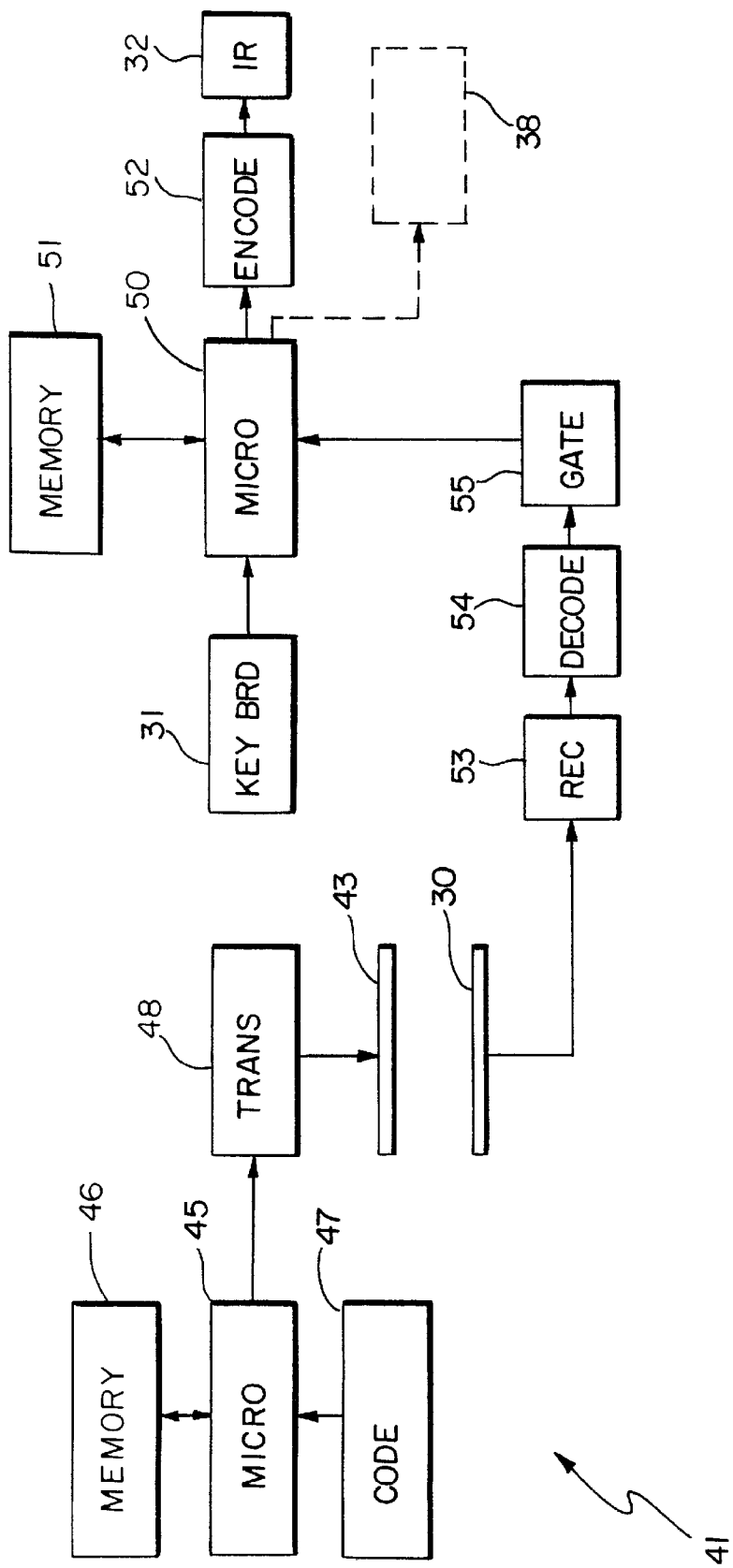
FIG. 3 sets forth a block diagram of the operative circuitry within the present invention toy device.

FIG. 3 sets forth a block diagram of the present invention toy device. Toy device 10 includes a circuit 41 supported within wrist unit 11 in the manner set forth above in FIG. 2. Thus, circuit 41 includes a microprocessor 45 having an associated memory 46. A code generating circuit 47 is also coupled to microprocessor 45. Microprocessor 45 is operatively coupled to a transmitting circuit 48 which in turn is coupled to contact 43.

FIG. 3 further shows the operative circuitry within device 12 set forth above in FIG. 1. Device 12 includes a microprocessor 50 having an associated memory 51 and a keyboard 31 coupled thereto. A contact 30 which, as is better seen in FIG. 1, is supported upon device 12 is coupled to a receiver 53 which in turn is coupled to a decoding circuit 54. Decoding circuit 54 controls a gate circuit 55 which provides and enabling signal to microprocessor 50. The output to microprocessor 50 is coupled to an infrared signal encoder 52 which in turn is coupled to an infrared transmitter 32.

In operation, microprocessor 45 operating in accordance with the stored instruction set or program within memory 46, receives a coded number sequence from code circuit 47 which is applied to the modulating input of transmitter 48. Transmitter 48 provides an output signal such as a radio frequency signal having the code received from code circuit 47 modulated thereon. Correspondingly, contact 43 is energized by transmitter 48 and, as is described above, is operatively coupled to the user's body.

At device 12, a receiving function is carried forward as contact 30 is touched by user 20 (seen in FIG. 1) coupling a portion of the energy within the user's body received from transmitter 48 and contact 43. The coupled signal and its modulated code are applied to a receiver 53 which recovers the coded information therefrom and applies it to decode circuit 54. Decode circuit 54 compares the coded signal to a stored reference signal and if a correct match is found energizes gate 55. Gate 55 when energized produces an enabling signal to microprocessor 50 causing microprocessor 50 to activate encoder 52 which in turn drives infrared output device 32.

If however the coded signal received by decode circuit 54 does not match the stored reference signal, gate 55 is not enabled. Accordingly, microprocessor 50 does not receive an enabling signal and keyboard inputs at keyboard 31 are not operatively coupled to encoder 52 and infrared transmitter 32. As a result, device 12 does not respond to the user.

The circuit shown in FIG. 3 for device 12 is substantially the same as the internal circuit within device 34 with the difference being found in the replacement of encoder 52 and infrared transmitting device 32 with a conventional sound circuit 38 (shown in dashed-line). In all other respects, the circuit within device 34 (seen in FIG. 1) is identical to the circuit shown in FIG. 3 as found within device 12.

Figure 4:
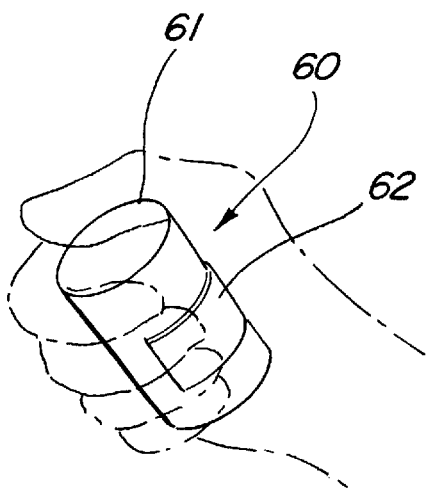
FIG. 4 sets forth a perspective view of an alternate embodiment of the present invention toy device.

FIG. 4 sets forth a perspective view of an alternate embodiment of the present invention. The embodiment shown in FIG. 4 differs from the previously described embodiment in that it is configured to be handheld as opposed to worn upon the users wrist. In all other respects however, the embodiment shown in FIG. 4 will be understood to be identical to the embodiment described above and will be understood to include circuit 41 operable in the same manner as described above within wrist unit 11. Thus, a handheld unit 60 includes a housing 61 which supports circuit 41 (seen in FIG. 3) together with a body contact 62. As seen in FIG. 4, the user hold unit 60 such that contact 62 touches the user's body such as the palm of a hand or the like allowing the signal to propagate from unit 60 through the user's body.

What has been shown is a toy device using through-the-body communication to activate a cooperating toy or other device through the propagation of an identifying encoded signal through the user's body. The encoded signal is produced by a wrist unit which is worn in much the same way as a conventional watch.

While particular embodiments of the invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention.

That which is claimed is:

1. A toy device comprising:
   a wrist unit having a housing, a first body contact and a wrist band;
   a transmitting circuit supported within said housing and having means for generating and coupling an encoded signal to said first body contact;
   a toy having a second body contact and an operable toy system; and
   a receiving circuit supported by said toy and having means for receiving and decoding an signal coupled to said second body contact and having decode means for enabling said operable toy system in response to receiving said encoded signal when a user wearing said wrist unit touches said second body contact,
   said encoded signal being propagated through a users body when wearing said wrist unit.

2. The toy device set forth in claim 1 wherein said encoded signal is a radio frequency signal.

3. A toy device comprising:
   a radio frequency transmitter having means for producing an encoded radio frequency signal and having means for coupling said signal to a user's body;
   a radio frequency receiver having means for receiving said radio frequency signal when touched by a user and for producing an enable signal; and
   a toy having said radio frequency receiver therein having operating means responsive to said enable signal; and
   a housing supporting said radio frequency transmitter such that said means for coupling is in contact with a user's body,
   said radio frequency signal being propagated through the body of a user.

4. The toy device set forth in claim 3 wherein said housing is a wrist unit having means for being worn upon a user's wrist.

5. The toy device set forth in claim 3 wherein said housing is configured to be held in a user's hand.

\* \* \* \* \*